United States Patent [19]

Scholl et al.

[11] Patent Number: 4,552,946

[45] Date of Patent: Nov. 12, 1985

[54] PROCESS FOR THE PRODUCTION OF POLYISOCYANATES CONTAINING ISOCYANURATE GROUPS, THE COMPOUNDS WHICH MAY BE OBTAINED ACCORDING TO THIS PROCESS, AND THE USE THEREOF FOR THE PRODUCTION OF POLYURETHANES

[75] Inventors: Hans-Joachim Scholl; Josef Pedain; Bernd Riberi, all of Cologne; Gerhard Mennicken, Leverkusen, all of Fed. Rep. of Germany

[73] Assignee: Bayer Aktiengesellschaft, Leverkusen, Fed. Rep. of Germany

[21] Appl. No.: 571,982

[22] Filed: Jan. 19, 1984

[30] Foreign Application Priority Data

Feb. 1, 1983 [DE] Fed. Rep. of Germany ....... 3303221

[51] Int. Cl.$^4$ .................................................. C08G 18/76
[52] U.S. Cl. ...................................... 528/67; 544/193; 544/222; 528/45
[58] Field of Search .................. 544/193, 222; 528/45, 528/67

[56] References Cited

U.S. PATENT DOCUMENTS

| | | | |
|---|---|---|---|
| 3,648,979 | 2/1972 | Liebsch et al. | 544/193 |
| 4,038,239 | 7/1977 | Coyner et al. | 528/67 |
| 4,111,914 | 9/1978 | Kresta | 528/48 OR |
| 4,115,373 | 9/1978 | Henes et al. | 528/48 |
| 4,129,554 | 12/1978 | Karasawa et al. | 528/48 |
| 4,145,544 | 3/1979 | Kuehn | 544/193 |
| 4,255,569 | 3/1981 | Müller et al. | 544/193 |
| 4,288,586 | 9/1981 | Bock et al. | 528/67 |
| 4,293,680 | 10/1981 | Mazanek et al. | 544/193 |
| 4,306,051 | 12/1981 | Gras et al. | 528/67 |
| 4,324,879 | 4/1982 | Bark et al. | 528/45 |
| 4,379,905 | 4/1983 | Stemmler et al. | 528/73 |
| 4,419,513 | 12/1983 | Bredenbach | 544/222 |
| 4,469,867 | 9/1984 | Disteldorf et al. | 544/222 |

FOREIGN PATENT DOCUMENTS

| | | |
|---|---|---|
| 0078991 | 5/1983 | European Pat. Off. |
| 2616415 | 11/1977 | Fed. Rep. of Germany |
| 1458564 | 6/1974 | United Kingdom |
| 1571933 | 7/1980 | United Kingdom |

OTHER PUBLICATIONS

Polyurethane Chem. Tech. Part I, pp. 94 et Seq., (1962).

*Primary Examiner*—John Kight
*Assistant Examiner*—Garnette D. Draper
*Attorney, Agent, or Firm*—Gene Harsh; Joseph C. Gil; Thomas W. Roy

[57] ABSTRACT

This invention relates to a new process for the production of polyisocyanates containing isocyanurate groups by partial trimerization of the isocyanate groups of organic polyisocyanates comprising (a) compounds or mixtures of compounds corresponding to the formula

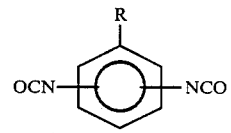

wherein R represents a saturated, aliphatic hydrocarbon radical having from 8 to 15 carbon atoms, and optionally (b) up to about 95 NCO equivalent %, based on the total of (a)+(b), of other organic polyisocyantes.

This invention also relates to the compounds which may be obtained according to this process and to the use thereof for the production of isocyanate-polyaddition products such as polyurethanes.

16 Claims, No Drawings

PROCESS FOR THE PRODUCTION OF POLYISOCYANATES CONTAINING ISOCYANURATE GROUPS, THE COMPOUNDS WHICH MAY BE OBTAINED ACCORDING TO THIS PROCESS, AND THE USE THEREOF FOR THE PRODUCTION OF POLYURETHANES

BACKGROUND OF THE INVENTION

1. Field of the Invention

This invention relates to a new process for the production of polyisocyanates containing isocyanurate groups by partial trimerization of the isocyanate groups of organic polyisocyanates with the (simultaneous) use of certain alkyl-substituted phenylene diisocyanates as starting polyisocyanate. This invention also relates to the compounds which may be obtained according to this process and to the use thereof for the production of isocyanate-polyaddition products such as polyurethanes.

2. Description of the Prior Art

A large number of processes for the production of polyisocyanates containing isocyanurate groups are known (J. H. Saunders and K. C. Frisch, Polyurethanes Chemistry and Technology, Part I, P. 94 et seq [1962]). In these processes, trimerization catalysts of the most varied type, stated by way of example in the above-mentioned reference, are used. In addition to the trimerization catalysts which are disclosed by way of example in the above-mentioned reference, the following have more recently proved to be universally usable trimerization catalysts: in particular Mannich bases (DE-OS No. 2,551,634 or DE-OS No. 2,641,380) for the trimerization of aromatic isocyanates, quaternary hydroxyalkyl ammonium hydroxides (EP-PS No. 37 65, U.S. Pat. No. 4,288,586, EP-PS No. 10 589 or U.S. Pat. No. 4,324,879) for the trimerization of aliphatic or cycloaliphatic polyisocyanates or complexed basic sodium or potassium compounds (DE-OS No. 3,100,262 or DE-OS No. 3,100,263). The processes and catalysts described in DE-OS No. 2,616,415 and DE-OS No. 2,616,416 are also very suitable.

An important area of use for the previously known polyisocyanates containing isocyanurate groups is the use thereof as reaction components in two-component polyurethane lacquers in combination with reaction components containing hydroxyl groups, for example combined with polyhydroxy-polyacrylates, polyhydroxypolyesters or alkyd resins containing hydroxyl groups.

However, most known polyisocyanates which contain isocyanurate groups still suffer from a number of disadvantages which are worth improving. Thus, the prior art polyisocyanates containing isocyanurate groups can only be diluted with difficulty using non-polar lacquer solvents, for example aliphatic or aromatic hydrocarbons. This disadvantage is manifested by the fact that when the polyisocyanates containing isocyanurate groups are mixed with aliphatic or aromatic hydrocarbons or with polyesters, polyacrylates or alkyd resins which are dissolved in these solvents, cloudiness and precipitation occur which render the production of lacquers impossible.

Another disadvantage of the prior art polyisocyanates containing isocyanurate groups is to be attributed to the frequently occurring incompatibility thereof with other binders and reaction components, which is manifested in a frequently too short processing time of the ready-for-use lacquer mixtures. The reason for this frequently too short processing time is attributed in particular to the fact that with the formation of only a few urethane groups in the ready-for-use lacquers, the solubility or compatibility which is poor anyhow becomes even poorer and the binder precipitates from the lacquer solution. The obvious idea of overcoming the poor compatibility by the simultaneous use of polar solvents results in a considerable increase in the price of the lacquers. The modification of the polyisocyanates with fatty alcohols which is recommended in DE-AS No. 2,414,413 implies a substantial improvement, but it has the disadvantage that due to this modification, isocyanate groups are used up which are no longer available for the formation of cross-linking points and which reduce the functionality of the polyisocyanates.

Therefore, an object of the present invention is to provide new, easily accessible polyisocyanates which contain isocyanurate groups; are compatible with slightly polar solvents and diluents; are miscible with hydroxyl-polyesters, hydroxyl-polyacrylates and hydroxylalkyd resins without clouding, even in the presence of non-polar solvents; and which have an improved processing time in admixture with these reaction components.

This object may be achieved by the process according to the present invention which is described in more detail in the following.

SUMMARY OF THE INVENTION

The present invention provides a process for the production of polyisocyanates containing isocyanurate groups by trimerizing a portion of the isocyanate groups of organic polyisocyanates in the presence of trimerization catalysts and by terminating the trimerization reaction at the degree of trimerization which is required in each case by adding a catalyst poison and/or by thermal decomposition of the trimerization catalyst which is used, characterized in that (a) compounds or mixtures of compounds corresponding to the formula

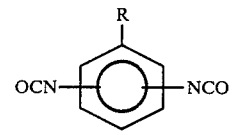

wherein R represents a saturated, aliphatic hydrocarbon radical having from 8 to 15 carbon atoms, and optionally (b) up to about 95 NCO equivalent %, based on the total of (a)+(b), of other organic polyisocyanates are used as the polyisocyanates to be trimerized.

The present invention also provides the polyisocyanates containing isocyanurate groups which may be obtained according to this process.

Furthermore, this invention provides the use of the polyisocyanates containing isocyanurate groups which may be obtained according to this process, optionally in a form free of excess starting polyisocyanates and/or optionally in a form blocked with isocyanate group blocking agents, as the isocyanate component for the production of isocyanate-polyaddition products such as polyurethanes.

DETAILED DESCRIPTION OF THE INVENTION

In the process according to the present invention, diisocyanates corresponding to the above-mentioned general formula are used as starting components (a) which is essential to the present invention, wherein R is as defined above. Preferred polyisocyanates are those which are present as a homologue and isomer mixture, and for which R represents a saturated, straight-chain, aliphatic hydrocarbon radical having from 8 to 15, in particular from 10 to 13 carbon atoms. The production of these preferred or more preferred diisocyanates to be used as the starting component (a) essential to the present invention is described in, for example EP-OS No. 58 368 or in DE-OS No. 3,105,776. In particular, the diisocyanates which are described in the above-mentioned European Patent Publication are the preferred starting materials (a) according to the present invention. In addition to these preferred or more preferred starting materials (a), those diisocyanates corresponding to the above-mentioned general formula may also be used as starting components (a) in the present process, for which R represents a branched aliphatic hydrocarbon radical having from 8 to 15 carbon atoms. They are prepared, for example, according to U.S. Pat. No. 2,986,576.

In the process according to the present invention, the component (a) essential to the invention is used either as a starting component on its own or together with up to about 95 NCO equivalent %, based on all the isocyanate groups of the starting polyisocyanates, of other polyisocyanates (b).

These polyisocyanates (b) which may optionally be simultaneously used include the following, for example:

(b1) aromatic polyisocyanates having a molecular weight above 173, preferably from 174 to 250, for example 2,4- or 2,6-toluylenediisocyanate, 2,4'-diphenylmethanediisocyanate, 4,4'-diphenylmethanediisocyanate, naphthylene-1,5-diisocyanate, 4,4',4''-triisocyanatotriphenyl-methane, 2,4,6-triisocyanatotoluene or polyphenyl-polymethylene-polyisocyanates, as they are produced by aniline-formaldehyde condensation and subsequent phosgenation ("crude MDI");

(b2) aliphatic or cycloaliphatic polyisocyanates having a molecular weight of above 139, preferably from 140 to 250, for example tetramethylenediisocyanate, hexamethylenediisocyanate, dodecamethylenediisocyanate, cyclobutane-1,3-diisocyanate, cyclohexane-1,3- and 1,4-diisocyanate, 1-isocyanato-3,3,5-trimethyl-5-isocyanatomethylcyclohexane(IPDI), perhydro-2,4- and/or -2,6-diisocyanatotoluene or perhydro-2,4'- and/or -4,4'-diisocyanatodiphenylmethane; or (b3) NCO prepolymers which have an NCO content of from about 1 to about 11% by weight and are based on (i) the diisocyanates (a) essential to the invention and/or the polyisocyanates mentioned under (b1) and (b2), and (ii) the polyhydroxyl compounds which are known from polyurethane chemistry in particular for two-component polyurethane lacquers and which have a molecular weight range of from about 62 to 5,000, preferably from about 200 to 2,000 of the type disclosed by way of example in U.S. Pat. No. 4,289,813, herein incorporated by reference, at column 3, line 47 to column 4, line 12.

Any mixtures of the polyisocyanates which are mentioned by way of example under (b1) to (b3) may also be used in the present process as component (b). The aromatic diisocyanates which are mentioned by way of example under (b1) are preferably used. 2,4-diisocyanatotoluene or commercial mixtures thereof with up to 35% by weight of 2,6-diisocyanatotoluene, based on the total quantity of the diisocyanatotoluene isomers, are particularly preferred components (b).

According to a preferred embodiment of the present process, from 5 to about 70 equivalent % of the starting components (a), in particular of the starting components (a) which are characterized as being preferred, based on all the isocyanate groups of the starting polyisocyanates, are used together with from about 30 to 95 NCO equivalent % of the starting component (b), in particular of the more preferred component (b).

All known prior art trimerization catalysts are included as trimerization catalysts, as they are stated by way of example in the above-mentioned publications. Trimerization catalysts which are particularly preferred are the Mannich bases which are described, for example in DE-OS No. 2,551,634, the quaternary hydroxy alkyl ammonium hydroxides which are described, for example in U.S. Pat. Nos. 4,324,879 or 4,288,586, the complexed basic sodium or potassium compounds which are described, for example in German Offenlegungsschrift Nos. 3,100,262 or 3,100,263, or the triazine salts which are described, for example in German Offenlegungsschrift Nos. 2,616,415 and 2,616,416.

The trimerization reaction according to the present invention is either stopped thermally, if thermally labile trimerization catalysts are used, or preferably by adding catalyst poisons of the type mentioned by way of example in the last-mentioned publications.

The process according to this invention may be carried out without solvent or in the presence of inert solvents and diluents. The following may be used as inert solvents: non-polar diluents, such as toluene, xylene, comparatively high molecular weight aromatic compounds, light petrol, mineral spirits and $C_{12}$–$C_{20}$ alkyl sulphonic acid esters, but also inert polar solvents, such as esters and ketones or mixtures of such solvents.

Mixtures of aromatic hydrocarbons and esters are preferred solvents, for example a mixture of butylacetate and xylene.

The trimerization reaction according to the present invention is generally carried out within a temperature range of from about 10° to 100° C., preferably from about 20° to 80° C. The optimum reaction temperature depends on the type of starting polyisocyanates and trimerization catalysts which are used, and may be determined by a simple preliminary experiment.

The trimerization reaction of the present invention is generally terminated upon reaching a degree of trimerization (degree of trimerization=percentage of the trimerized isocyanate groups, based on the total quantity of the isocyanate groups present in the starting polyisocyanate) of from about 10 to 70%. The course of the reaction may be followed, for example by continuously determining the refractive index.

If the present process is carried out without solvent, optionally with the subsequent removal of excess starting isocyanate, for example in a thin layer evaporator, the degree of trimerization is generally from about 10 to 40%. If the present process is carried out in the presence of solvents without subsequent removal of unreacted starting isocyanate, the degree of trimerization is generally from about 50 to 70%.

It is a particular advantage of the present process that, at a degree of trimerization of from about 50 to 70%, the content of monomeric isocyanates is surprisingly very low, and a subsequent removal of monomeric isocyanates by extraction or distillation is unnecessary.

The trimerization reaction is terminated, as already explained, by thermal or chemical deactivation of the catalyst.

In the process of the present invention, when starting components (b) are simultaneously used, previously produced mixtures of components (a) and (b) are preferably used. According to one particular embodiment of the present process, it is, however, also possible to initially trimerize in a first reaction step some, i.e., a maximum quantity of about 30%, preferably a maximum quantity of about 5% of the isocyanate groups of component (a) or of component (b), and then add the remaining component to the reaction mixture.

However, in such a case, care must be taken that the trimerization reaction ends at the earliest when, after the addition of the remaining starting component, a further 5%, preferably a further 10%, based on all the isocyanate groups which were originally present in all of the starting polyisocyanates, have been trimerized. Thus, for example, it is possible to trimerize a maximum of 30 NCO equivalents from 100 NCO equivalents of component (a) or (b), to then incorporate into the reaction mixture, 100 NCO equivalents of the remaining component, to continue the trimerization reaction and, in the case when 30 NCO equivalents of the first starting component were initially trimerized, to terminate the reaction at the earliest after the trimerization of a total of 20% preferably 25%, of the total number of NCO equivalents have been trimerized.

Particularly if the present process is carried out without solvent, the products of this process may be freed from excess, unreacted starting isocyanates in a known manner, for example by thin layer distillation or extraction, so that polyisocyanates containing isocyanurate groups, with a content of monomeric starting isocyanates of less than about 3% by weight, preferably less than about 0.7% by weight may be obtained.

Excess starting isocyanates are preferably removed if the products of the process are intended to be used for the production of lacquers, for example polyurethane lacquers. Before they are used as an isocyanate component in these two-component lacquers, the products of the present process may be modified, for example by the introduction of urethane, urea, biuret or allophanate groups.

Of course, it is also possible to use the products of the present process without removing excess starting isocyanates, for example for the production of foams, for example polyurethane foams.

The products of the present process may of course be blocked in a known manner with suitable isocyanate group blocking agents, for example phenol, ε-caprolactam, malonic acid diethyl ester or acetoacetic ester.

The products of the present process or derivatives thereof which are obtained by the mentioned blocking reaction are valuable starting materials in the production of plastics, for example polyurethane plastics, according to the isocyanate-polyaddition process by reaction with compounds containing isocyanate-reactive hydrogens. They are particularly suitable as the isocyanate component in two-component lacquers, for example polyurethane lacquers.

The following Examples illustrate the present invention. All the percentages relate to % by weight, unless otherwise indicated. All the "parts" relate to parts by weight. All the quantities in "NCO equivalent %" relate to the total quantity of the starting isocyanates which are used in the Examples.

EXAMPLES

In the following production Examples 1–37, the diisocyanate mixture according to Example 1 of EP-A No. 58 368 and U.S. Pat. No. 4,394,495 which is distilled under a pressure of 2.2 mbar and within a temperature range of from 185° to 203° C. is used as "diisocyanate I".

"Catalyst A" is a mixture of the compounds

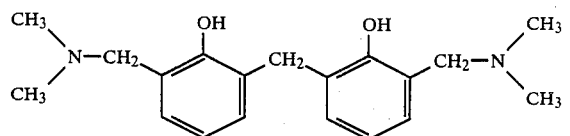

and

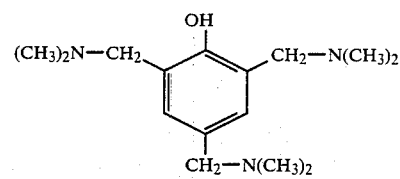

in a ratio of 1:2.75.

"Catalyst B" essentially consists of the Mannich base

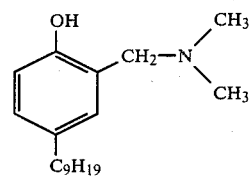

These catalysts were produced according to the teachings of DE-OS No. 2,551,634.

EXAMPLE 1

800 parts of a mixture of 98% of 2,4-toluylenediisocyanate and 2% of 2,6-toluylenediisocyanate and 200 parts of diisocyanate I (7.1 NCO equivalent %) were dissolved under nitrogen in 1,000 parts of a mixture of xylene and butyl acetate (weight ratio 1:1) in a three-necked flask equipped with a stirrer, a dropping funnel, an internal thermometer and a bubble counter, heated to 50° C. with stirring and mixed with 0.4% by weight of catalyst (A), based on the isocyanate which is used. The slowly starting trimerization reaction was maintained at 50° C. for 30 hours. Thereafter, the NCO content had fallen to 7.9%. The reaction was stopped by adding 0.5% by weight of toluene sulphonic acid methyl ester, based on the isocyanate which was used, and the reaction mixture was restirred for 1 hour at 50° C. A polyisocyanate mixture containing isocyanurate groups was obtained as a clear, colorless solution, having the following data: NCO content: 7.9%; free toluylene diisocyanate: 0.15%; free diisocyanate I: 0.29%; viscosity (23° C.): 1100 mPas.

Examples 2 to 9 which are listed in Table I were carried out according to Example 1.

The resulting polyisocyanates of Examples 1 to 9 having a low monomer content and containing isocyanurate groups are suitable for the production of PUR lacquers.

TABLE 1

| | Quantities Used Isocyanates | | | Product data | | | | Toluylene diisoc./ | |
|---|---|---|---|---|---|---|---|---|---|
| | Toluylene- | Diisocyanate I | | | | | | diisoc. (I) | Viscos. |
| Example | diisoc. 2,4-2,6-t. | (parts) | NCO-equivalent % | Solvent | Cat. A | Cat. B | % NCO | (% residual amounts) | 23° C./ mPa · s |
| 2 | 900 | — | 100 | 5.6 | xylene/butyl-lac. 1:1 | 0.4 | — | 8.6 | 0.26/0.17 | 2200 |
| 3 | 850 | — | 150 | 8.7 | xylene/butyl-lac. 1:1 | 0.4 | — | 8.75 | 0.31/0.1 | 2220 |
| 4 | 800 | 75 | 125 | 7.1 | xylene/butyl-lac. 1:1 | 0.4 | — | 8.2 | 0.13/0.18 | 1400 |
| 5 | 825 | 25 | 150 | 8.7 | xylene/butyl-lac. 1:1 | 0.4 | — | 8.3 | 0.22/0.25 | 700 |
| 6 | 800 | 25 | 175 | 10.2 | xylene/butyl-lac. 1:1 | 0.4 | — | 8.0 | 0.21/0.38 | 1000 |
| 7 | 720 | 180 | 100 | 5.6 | butylacetate | 0.4 | — | 9.0 | 0.3/0.3 | 400 |
| 8 | 800 | — | 200 | 11.8 | ethylacetate | 0.4 | — | 6.1 | 0.57/0.12 | 50 |
| 9 | 450 | 50 | 500 | 35.2 | light petrol/ Solvesso* 100 1:1 | 0.4 | 0.4 | 6.4 | 0.26/0.27 | 1600 |

All the products are clear, colorless or pale yellow solutions.
*Solvesso 100 is a standard mixture of alkyl aromatic compounds having a boiling range which lies above the boiling point of xylene.

The following Examples 10 and 11 describe the process according to the present invention during the production of polyisocyanate mixtures containing isocyanurate groups which are suitable for foamed polyurethanes.

EXAMPLE 10

0.1% by weight of catalyst (B) was added according to Example 1 to a mixture of 500 parts of toluylene diisocyanate (80% of 2,4- and 20% of 2,6-isomer) and 500 parts of diisocyanate I (35.2 NCO equivalent %), at 50° C. and with stirring. The mixture was stirred for 5 hours at 50° C., and thereafter the NCO content had fallen to 28.7%. The reaction was stopped using 0.1% by weight of toluene sulphonic acid methyl ester, and the reaction mixture was restirred for 1 hour at 50° C.

A clear solution of the polyisocyanate mixture containing isocyanurate groups was obtained, having the following data: NCO content: 28.7%; free toluylene diisocyanate: 26.8%; free diisocyanate I: 30.2%; viscosity (23° C.): 1100 mPas.

EXAMPLE 11

Example 10 was repeated with the difference that 500 parts of toluylene diisocyanate were pretrimerized with 0.1% by weight of catalyst to an NCO content of 34%, and 500 parts of diisocyanate I were then metered in over a period of 15 minutes. The mixture was restirred for 30 minutes at 50° C., and then the trimerization reaction was stopped and a polyisocyanate mixture having the following data was obtained: NCO content: 28.8%; free toluylenediisocyanate: 18.9%; free diisocyanate I: 40.3%; viscosity (23° C.): 1200 mPas.

EXAMPLE 12

500 parts of 4,4'-diisocyanatodiphenylmethane and 500 parts of diisocyanate I (corresponding to 38 NCO equivalent %) were reacted according to Example 10. A solids-free polyisocyanate mixture was obtained having the following data: NCO content: 23.7%, viscosity (23° C.) : 9000 mPas.

EXAMPLE 13

The process was carried out as stated in Example 1, and 500 parts of diisocyanate I were trimerized with 0.8% by weight of catalyst A and 0.1% by weight of catalyst B at from 50° to 60° C. over a period of 45 hours in 500 parts of mineral spirits (boiling range 155°–185° C.). A clear, colorless approximately 50% solution was obtained having an NCO content of 6.9%. The solution still contained 3.2% of unreacted diisocyanate.

In comparison herewith, when it was attempted to trimerize a mixture (80:20) of 2,4- and 2,6-toluylene diisocyanate, cloudiness occurred after a short time. The solution became inhomogeneous and formed two phases.

EXAMPLE 14

150 parts of diisocyanate I and 850 parts of 2,4-toluylene diisocyanate were mixed and reacted at 80° C. with 100 parts of a hydroxyl-polyester of adipic acid, hexanediol-1,6 and neopentyl glycol (molar ratio of diols, 65:35) having a molecular weight of about 1700, until practically all of the OH groups had been converted. The reaction product thus obtained contained 8.4 NCO equivalent % of free diisocyanate I, 90.5 NCO equivalent % of free toluylene diisocyanate and 1.1 NCO equivalent % of NCO prepolymer which has formed from diisocyanate I, toluylene diisocyanate and hydroxyl-polyester. The product was then dissolved in 1100 parts of a mixture of xylene/butylacetate 1:1 and the process was further carried out as described in Example 1 by maintaining the solution at 50° C. and adding 0.5% by weight of catalyst A (based on the diisocyanate mixture which was used). The reaction was stopped after 25 hours at this temperature by adding 0.5% by weight of p-toluene sulphonic acid methyl ester (also based on the diisocyanate mixture).

A clear, practically colorless, approximately 50% solution was obtained having an NCO content of 7.7% and a viscosity of 900 mPas/23° C. The residual content in the solution of diisocyanate mixture was 0.8%.

EXAMPLE 15

In this Example, some polyisocyanates produced according to the present process were used as hardeners for a two-component PUR wood lacquer.

The products are combined with a polyester component (alkyd resin type). This alkyd resin is produced by the melt condensation of 30 parts of peanut oil fatty acid, 32 parts of triethylene glycol and 35 parts of phthalic acid anhydride. It has a hydroxyl number of 150, an acid number of 8 and is dissolved 75% in xylene.

The hardeners produced according to the process of the present invention were compared with a standard hardener ($H_O$), according to the prior art which was produced analogously to Example 1 by the trimerization of 2,4-toluylene diisocyanate in 50% butylacetate solution. (A production in xylene/butylacetate in contrast to the present process is impossible, because in that case an inhomogeneous, cloudy solution was produced). The 50% solution of the Comparative Hardener had an NCO content of 7.7% and a viscosity of 700 mPas/23° C.

In order to provide an effective comparison, a weight ratio of alkyd resin:hardener was selected as 60:40 (solid/solid). An NCO:OH ratio of about 1 was observed. All the lacquer solutions were adjusted with butylacetate to 45% solids.

Drying Rate

In order to test the drying rate, films were applied to glass in each case in thicknesses of 90 μm, 150 μm and 210 μm using a coating roller system. The sand drying and the hand drying time were determined.

The result is given in Table II.

For all the lacquers, drying was very fast, just as fast as, or faster than with the standard hardener $H_O$. No substantial difference may be established between the drying times of individual products.

TABLE II

| Lacquer Mixture with Hardener | Film Thickness | Sand Drying* (min.) | Hand Drying* (min.) |
|---|---|---|---|
| $H_1$ (Example 1) | 90 μm | 7 | 10 |
|  | 150 μm | 10 | 14 |
|  | 210 μm | 13 | 20 |
| $H_2$ (Example 2) | 90 μm | 7 | 9 |
|  | 150 μm | 11 | 13 |
|  | 210 μm | 13 | 20 |
| $H_3$ (Example 3) | 90 μm | 6 | 10 |
|  | 150 μm | 10 | 15 |
|  | 210 μm | 12 | 24 |
| $H_4$ (Example 5) | 90 μm | 5 | 9 |
|  | 150 μm | 9 | 13 |
|  | 210 μm | 10 | 18 |
| $H_5$ (Example 6) | 90 μm | 6 | 10 |
|  | 150 μm | 9 | 14 |
|  | 210 μm | 11 | 19 |
| $H_6$ (Example 8) | 90 μm | 7 | 9 |
|  | 150 μm | 10 | 13 |
|  | 210 μm | 12 | 19 |
| $H_7$ (Example 9) | 90 μm | 8 | 10 |
|  | 150 μm | 10 | 14 |
|  | 210 μm | 12 | 20 |
| $H_O$ (Comparative product) | 90 μm | 7 | 10 |
|  | 150 μm | 11 | 15 |
|  | 210 μm | 14 | 23 |

*Sand drying: Sand is sprinkled onto the lacquered plate. A waiting time of 1 minute elapses and an attempt is then made to remove the sand with a brush. The time after which the sand may be completely removed is stated as the drying time.
*Hand drying: An index finger is pressed onto the lacquer film. The period of time after which an impression no longer appears is specified.

Viscosity course/processing time:

The viscosity course of the lacquer mixtures was followed by means of the outflow time in a DIN-4 beaker (DIN 53211), (Table III).

TABLE III

| Lacquer mixture with hardener | Outflow time in a DIN-4 beaker (sec) | | | |
|---|---|---|---|---|
|  | after 0 h | after 4 h | after 6 h | after 8 h |
| $H_1$ | 18 | 36 | 92 | x |
| $H_2$ | 18 | 40 | 88 | x |
| $H_3$ | 19 | 42 | x | x |
| $H_4$ | 18 | 30 | 70 | x |
| $H_5$ | 20 | 30 | 64 | 99 |
| $H_6$ | 18 | 33 | 42 | 90 |
| $H_7$ | 18 | 30 | 40 | 88 |
| $H_O$ | 27 | x | x | x | x = Mixture gelatinizes

The viscosity of the lacquer mixture prepared with the hardeners which were produced according to the present process was lower than the viscosity of the lacquer mixture prepared with the Comparative Hardener immediately after the mixing of the reaction components. The reason for this obviously lies in the better compatibility of these hardeners with the other ingredients of the lacquer mixture. The lacquer mixture with the Comparative Hardener $H_O$ had gelatinized after just 70 minutes. However, the lacquer mixtures according to the process of the present invention may be used for practically one working day. They have an advantageously long processing time.

Furthermore, the hardness of the films was also tested by means of pendulum damping (DIN 53 157). After one day, all the lacquer films had, as in the case of the Comparative Experiment, a pendulum damping of from 120 to 140 s, and after 14 days, a damping of from 170 to 180 s.

The solvent resistance of all the films was also very good after 7 days.

EXAMPLE 16

Important binders for wood varnishing are nitrocellulose and cellulose acetobutyrate. Prior art aromatic isocyanates containing isocyanurate groups are incompatible with the two binders.

The hardeners $H_1$ to $H_6$ produced according to the present process were diluted with butylacetate to 25% solutions and then mixed with a 10% solution of collodium wood chips in butylacetate or with a 20% solution of a cellulose acetobutyrate type (Cellit BP 300) in a ratio (solid on solid) of 9:1, 8:2 and 7:3. All the solutions and the corresponding films were clear. $H_O$, as the Comparative Hardener, formed cloudy solutions and an unusable cloudy lacquer film with cellulose acetobutyrate. The solution was also slightly cloudy with nitrocellulose, but the film was clear.

Examples 17 to 21 describe how the process according to the present invention is carried out in a plasticizer. The products of the process are surprisingly effectively soluble in this medium as well. They may be used for the production of solvent-free lacquers.

EXAMPLE 17

1% by weight, based on the diisocyanate which was used, of catalyst (B) was added at 60° C., with stirring and under inert gas ($N_2$) to a solution of 250 parts of diisocyanate I in 705 parts of Mesamol ® plasticizer (manufacturer: Bayer AG, Leverkusen; PVC-plasticizer based on alkane sulphonic acid aryl ester). The mixture was stirred at 60° C. until an NCO value of 3.2% was attained (from about 4 to 6 hours). 0.5% by weight of p-toluene sulphonic acid methyl ester, based on the diisocyanate which is used, was slowly added and the mixture was restirred for 1 hour at 60° C. A clear solution was obtained having a viscosity of 275 mPas (23° C.).

Examples 18 to 21 which are listed in the following Table IV were carried out according to Example 17.

TABLE IV

| Ex. | Reaction temp. | Reaction time | Catalyst (B) (parts) | NCO (%) | Viscosity (23° C./mPas) |
|---|---|---|---|---|---|
| 18 | 60° C. | 70 min. | 1 | 3.6 | 275 |
| 19 | 60° C. | 7 h | 1.1 | 3.0 | 290 |
| 19 | 60° C. | 12 h | 1.3 | 2.8 | 320 |
| 21 | RT | 6 d | 1.4 | 2.5 | 400 |

Examples 22 to 28 describe how the process according to the present invention is carried out in substance (without the simultaneous use of other isocyanates). The products of the process are surprisingly non-crystalline liquids. They may be used for the production of solvent-free coatings.

EXAMPLE 22

100 parts of diisocyanate I were reacted with 0.35 parts of catalyst B at 60° C., with stirring and under inert gas ($N_2$) The mixture was stirred at 60° C. until an NCO value of 22.6% was attained (about 2 hours). 0.35 parts of p-toluene sulphonic acid methyl ester were slowly added and the mixture was restirred for 1 hour at 60° C. A clear liquid was obtained having a viscosity of 60 mPa.s (23° C.).

Examples 23 to 28 which are listed in the following Table V were carried out according to Example 22.

TABLE V

| Ex. | Reaction temp. | Reaction time | Catalyst (B) (parts) | NCO % | Viscosity (23° C./mPa · s) |
|---|---|---|---|---|---|
| 23 | 60° C. | 3 h | 0.35 | 21.1 | 300 |
| 24 | 60° C. | 5 h | 0.35 | 18.4 | 2,000 |
| 25 | 70° C. | 6 h | 0.35 | 16.1 | 22,500 |
| 26 | RT | 2 days | 0.55 | 17.7 | 3,700 |
| 27 | RT | 3 days | 0.55 | 15.6 | 38,000 |
| 28 | 70° C. | 8 h | 0.35 | 14.3 | 80,000 |

EXAMPLE 29

672 g (4 mols) of hexamethylenediisocyanate (HDI) and 260 g (0.8 mols) of diisocyanate I (NCO content of mixture: 43.3%) were reacted with 2 ml of a 0.5 molar solution of potassium acetate in polyethylene glycol (average molecular weight 370) with stirring and with the exclusion of moisture at 50° C. After a reaction time of 90 minutes, the initial refractive index: $n_D^{25} = 1.4696$ had risen to $n_D^{25} = 1.4850$. The reaction was terminated by adding 1 ml of a solution of perfluorobutenoic acid (10% by weight) in HDI. The mixture was restirred for 1 hour at 50° C., and a reaction product was obtained having an NCO content of 33.9% (degree of trimerization: 21.7%). After thin layer distillation, 381 g of a high viscosity, transparent resin was obtained having the following data: NCO content: 12.4%, free HDI: 0.25%, free diisocyanate I: <0.1%.

The amount of HDI incorporated in the trimer was 33.3%.

EXAMPLE 30

840 g (5 mols) of HDI and 162 g (0.5 mols) of diisocyanate I (NCO content of mixture: 45.6%) were reacted at 50° C. with 4 ml of catalyst N,N,N-trimethyl-N-(2-hydroxypropyl)-ammonium hydroxide solution (about 4% solution in ethylhexanol/methanol 8:1). After 2 hours at 50° C., the initial refractive index $n_D^{26°\ C.} = 1.4618$ had risen to $n_D^{26°\ C.} = 1.4790$. The reaction product was heated to 130° C. over a period of 15 minutes and was then stirred for 30 minutes at this temperature. Thereafter, the refractive index and the NCO content were constant: $n_D^{26°\ C.} = 1.4845$/NCO: 32.2% (degree of trimerization) 29.4%). After thin layer distillation, 490 g of a polyisocyanate mixture containing isocyanurate groups were obtained as a high viscosity, transparent resin having the following data: NCO-content: 15.5%, free HDI: 0.32%, free diisocyanate I<0.1%.

The amount of HDI incorporated in the resin was 67.7%.

EXAMPLE 31

840 g (5 mols) of HDI and 81 g (0.25 mols) of diisocyanate I (NCO content of mixture: 47.5%) were reacted according to Example 30 with 3.5 ml of catalyst until an NCO content of 32.2% was attained (degree of trimerization: 32.2%). After thin layer distillation, 494 g of product were obtained having the following data: NCO-content: 17.8%, free HDI: 0.51%, free diisocyanate I: <0.1% by weight, viscosity (23° C.): about 60,000 mPa.s, incorporated HDI: 84.1%.

EXAMPLE 32

1344 g (8 mols) of HDI (NCO content of mixture: 50%) were heated to 50° C. with stirring and with the exclusion of moisture, mixed with 6 ml of catalyst according to Example 30 and stirred for 1 hour at 50° C. Thereafter, the NCO content had fallen to 48.5% (degree of trimerization 3%). 260 g (0.8 mols) of diisocyanate I were then added dropwise at 50° C. over a period of 40 minutes. After a reaction time of 80 minutes, the reaction product was heated to 130° C. over a period of 15 minutes and was restirred at this temperature for 30 minutes. Thereafter, the refractive index and the NCO value were constant: $n_D^{24} = 1.4808$/NCO: 33.0% (degree of trimerization: 27.6%). After thin layer distillation, 698 g of a polyisocyanate mixture containing isocyanurate groups were obtained as a high viscosity, transparent resin having the following data: NCO content: 15.5%, free HDI: 0.37%, free diisocyanate I: <0.1%, incorporated HDI: 63.1%.

EXAMPLE 33

1344 g (8.0 mols) of HDI were reacted according to Example 32 with 6 ml of catalyst until the NCO content amounted to 48.7% (degree of trimerization 2.6%). Thereafter, 130 g (0.4 mols) of diisocyanate I were added dropwise over a period of 30 minutes. The process was carried out according to Example 33 until an NCO content of 34.5% was attained (degree of trimerization: 25.3%). After thin layer distillation, 713 g of product were obtained having the following data: NCO content: 18.0%, free HDI: 0.55%, free diisocyanate I: <0.1%, viscosity (23° C.): about 55,000 mPa.s, incorporated HDI: 82.1%.

EXAMPLE 34

1332 g (6 mols) of 3,5,5-trimethyl-1-isocyanato-3-isocyanato-methylcyclohexane (isophoronediisocyanate) and 97 g (0.3 mols) of diisocyanate I (NCO content of mixture: 37.0%) were mixed according to Example 30 with 16 ml of catalyst at from 60° to 70° C. over a period of 1 hour. The mixture was then stirred for 3 hours at 70° C. The reaction product was then heated to 130° C. over a period of 15 minutes and was stirred for 30 minutes at this temperature. Thereafter, the refractive index and the NCO content were constant: $n_D^{24}=1.4960$/NCO: 30.2% (degree of trimerization: 18.4%). After thin layer distillation, 262 g of a polyisocyanate containing isocyanurate groups were obtained having the following data: NCO content: 13.8%, free isophoronediisocyanate: 0.50%, free diisocyanate I: <0.1%, incorporated isophoronediisocyanate: 78.1%.

Appearance: brittle, clear resin.

EXAMPLE 35

900 parts of toluylenediisocyanate and 100 parts of diisocyanate I (5.6 NCO equivalent %) were dissolved in xylene/butylacetate according to Example 1, and mixed with 0.2% by weight of catalyst B at room temperature. The slowly starting trimerization reaction was maintained for 22 hours at room temperature. Thereafter the NCO content had fallen to 8.4%. The reaction was stopped by adding 0.2% by weight of toluene sulphonic acid methyl ester, and a clear solution was obtained having the following data: NCO content: 8.4%, free toluylene-diisocyanate 0.24%, free diisocyanate I: 0.1%, viscosity (23° C.): 2100 mPa.s.

EXAMPLE 36

Example 35 was repeated using the diisocyanate according to Example 6 of U.S. Pat. No. 2,986,576 having a branched alkyl chain. After the reaction had lasted for 30 hours at room temperature and was then stopped, a clear solution was obtained which had the following data: NCO content: 7.9%, free toluylenediisocyanate: 0.44%, free diisocyanate according to Example 6 of U.S. Pat. No. 2,986,576: 0.36%, viscosity (23° C.): 4700 mPa.s.

EXAMPLE 37

A clear solution was obtained with the simultaneous use of 0.3% by weight of catalyst B, according to Example 36, after a reaction lasting for 9 hours at room temperature which was stopped with 0.3% by weight of toluene sulphonic acid methyl ester. This solution had the following data: NCO content: 8.5%, free toluylenediisocyanate: 0.51%, free diisocyanate according to Example 6 of U.S. Pat. No. 2,986,576: >0.1%, viscosity (23° C.): 2400 mPa.s.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of polyisocyanates containing isocyanurate groups which comprises
(1) trimerizing a portion of the isocyanate groups of organic polyisocyanates in the presence of a trimerization catalyst, and
(2) terminating the trimerization reaction at the desired degree of trimerization by the addition of a catalyst poison or by thermal decomposition of the trimerization catalyst or a combination of both,
wherein said organic polyisocyanates comprise
(a) from about 5 to 100 NCO equivalent percent of a compound or mixture of compounds corresponding to the formula:

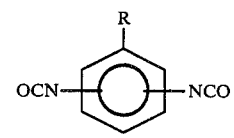

wherein R represents a saturated, aliphatic hydrocarbon radical having from 8 to 15 carbon atoms and
(b) up to about 95 NCO equivalent percent, of organic polyisocyanates other than those in (a), said NCO equivalent percent being based on the total number of isocyanate groups present in (a)+(b).

2. The process of claim 1 which comprises
(1) initially trimerizing up to 30 percent of the isocyanate groups of either polyisocyanate (a) or (b), and subsequently adding the remaining starting polyisocyanate to the reaction mixture, and
(2) terminating the trimerization reaction at the earliest when a further 5 percent of the isocyanate groups, based on all the isocyanate groups of the starting polyisocyanates (a) and (b), have been trimerized.

3. The process of claim 1 wherein the polyisocyanates (a) are present as a mixture of compounds.

4. The process of claim 1 wherein 2,4- or 2,6-diisocyanato-toluene or mixture thereof is used as polyisocyanate (b).

5. The process according to claim 1 wherein the starting polyisocyanates comprise
(a) from about 5 to 70 NCO equivalent percent of a mixture of diisocyanates which correspond to the formula set forth in claim 1 and
(b) from about 30 to 95 NCO equivalent percent of 2,4-diisocyanato-toluene or mixtures thereof with up to 65 percent by weight, based on the total quantity of the diisocyanato-toluene isomers, of 2,6-diisocyanato-toluene.

6. The process of claim 5 which comprises
(1) initially trimerizing up to 30 percent of the isocyanate groups of either polyisocyanate (a) or (b), and subsequently adding the remaining starting polyisocyanate to the reaction at the earliest mixture, and
(2) terminating the trimerization reaction when a further 5 percent of the isocyanate groups, based on all the isocyanate groups of the starting polyisocyanates (a) and (b), have been trimerized.

7. A polyisocyanate containing isocyanurate groups and prepared by a process which comprises (1) trimerizing a portion of the isocyanate groups of organic polyisocyanates in the presence of a trimerization catalyst, and
(2) terminating the trimerization reaction at the desired degree of trimerization by the addition of a catalyst poison or by thermal decomposition of the trimerization catalyst, or a combination of both wherein said organic polyisocyanates comprise
(a) from about 5 to 100 NCO equivalent percent of a compound or mixture of compounds corresponding to the formula:

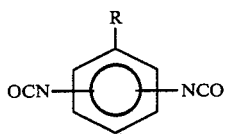

wherein R represents a saturated, aliphatic hydrocarbon radical having from 8 to 15 carbon atoms and
(b) up to about 95 NCO equivalent percent of organic polyisocyanates other than those in (a),
said NCO equivalent percent being based on the total number of isocyanate groups present in (a)+(b).

8. The polyisocyanate of claim 7 which prepared by
(1) initially trimerizing up to 30% of the isocyante groups of either polyisocyanate (a) or (b), and subsequently adding the remaining starting polyisocyanate to the reaction mixture, and
(2) terminating the trimerization reaction at the earliest when a further 5% of the isocyanate groups, based on all the isocyanate groups of the starting polyisocyanates (a) and (b), have been trimerized.

9. The polyisocyanate of claim 7 wherein the polyisocyanates (a) are present as a mixture of compounds.

10. The polyisocyanate of claim 7 wherein 2,4- or 2,6-diisocyanato-toluene or mixture thereof is used as polyisocyanate (b).

11. The polyisocyanate of claim 7 wherein the starting polyisocyanates comprise
(a) from about 5 to 70 NCO equivalent percent of a mixture of diisocyanates which correspond to the formula set forth in claim 12 and
(b) from about 30 to 95 NCO equivalent percent of 2,4-diisocyanate-toluene or mixtures thereof with up to 65% by weight, based on the total quantity of diisocyanato-toluene isomers, of 2,6-diisocyanato-toluene.

12. The polyisocyanate of claim 11 which is prepared by
(1) initially trimerizing up to 30% of the isocyanate groups of either polyisocyanate (a) or (b), and subsequently adding the remaining starting polyisocyanate to the reaction mixture, and
(2) terminating the trimerization reaction at the earliest when a further 5% of the isocyanate groups, based on all the isocyanate groups of the starting polyisocyanates (a) and (b), have been trimerized.

13. A process for the production of isocyanate-polyaddition products which comprises reacting
(a) the polyisocyanates of claim 11 and
(b) at least one compound containing isocyanate-reactive hydrogens.

14. The process of claim 7 wherein said polyisocyanates of step (a) are blocked with blocking agents.

15. The process of claim 7 wherein said isocyanate-polyaddition products are polyurethanes.

16. The process of claim 9 wherein said polyisocyanates of step (a) are blocked with blocking agents.

* * * * *